US010293516B2

(12) United States Patent
Pietarinen et al.

(10) Patent No.: US 10,293,516 B2
(45) Date of Patent: May 21, 2019

(54) FIBER BASED PRODUCT

(71) Applicant: UPM-KYMMENE CORPORATION, Helsinki (FI)

(72) Inventors: Suvi Pietarinen, Lappeenranta (FI); Sanna Valkonen, Lappeenranta (FI); Okko Ringena, Neusäss (DE)

(73) Assignee: UPM-KYMMENE CORPORATION, Helsinki (FI)

( * ) Notice: Subject to any disclaimer, the term of this patent is extended or adjusted under 35 U.S.C. 154(b) by 0 days.

(21) Appl. No.: 15/114,150

(22) PCT Filed: Jan. 27, 2015

(86) PCT No.: PCT/FI2015/050051
§ 371 (c)(1),
(2) Date: Jul. 26, 2016

(87) PCT Pub. No.: WO2015/114211
PCT Pub. Date: Aug. 6, 2015

(65) Prior Publication Data
US 2017/0001329 A1    Jan. 5, 2017

(51) Int. Cl.
*B27N 3/00* (2006.01)
*B27N 3/18* (2006.01)
(Continued)

(52) U.S. Cl.
CPC .............. *B27N 3/002* (2013.01); *B27N 3/18* (2013.01); *C08L 97/005* (2013.01); *C08L 97/02* (2013.01);
(Continued)

(58) Field of Classification Search
CPC ......... B27N 3/002; B27N 3/18; C08L 97/005; C08L 97/02; C09D 197/005; G01N 21/293; G01N 21/5907; G01N 21/8803
See application file for complete search history.

(56) References Cited

U.S. PATENT DOCUMENTS

| 4,250,382 A | 2/1981 | Libby |
| 2003/0203998 A1 | 10/2003 | Gres |

(Continued)

FOREIGN PATENT DOCUMENTS

| CN | 101469258 A | 7/2009 |
| CN | 102352200 A | 2/2012 |

(Continued)

OTHER PUBLICATIONS

Tolbert, et al. "Characterization and analysis of the molecular weight of lignin for biorefining studies", 2014 Society of Chemical Industry and John Wiley & Sons, Ltd., Biofuels, Bioprod. Bioref.
(Continued)

*Primary Examiner* — Robert S Walters, Jr.
(74) *Attorney, Agent, or Firm* — Nixon Peabody LLP

(57) ABSTRACT

The invention relates to a method for producing a fiber based product, wherein the method comprises the steps of: a) applying a binder composition over a at least one surface of at least one fiber based substrate; b) determining the distribution of the applied binder composition over the en-tire at least one surface of the at least one fiber based substrate; and c) based on the determination in step b) either accepting the treated at least one fiber based substrate for the production of the fiber based product or rejecting the treated at least one fiber based substrate from the production of the fiber based product. The invention further relates to a method for producing a binder composition, to a binder composition and to a fiber based product.

5 Claims, 1 Drawing Sheet

Apply binder composition over a surface of the fiber based substrate — a)

Determine the distribution of the applied binder composition over the surface — b)

Accept the treated substrate for the production or reject the treated substrate from the production of the fiber based product — c)

(51) Int. Cl.
*C08L 97/00* (2006.01)
*C08L 97/02* (2006.01)
*G01N 21/29* (2006.01)
*G01N 21/59* (2006.01)
*C09D 197/00* (2006.01)
*G01N 21/88* (2006.01)

(52) U.S. Cl.
CPC ....... *C09D 197/005* (2013.01); *G01N 21/293* (2013.01); *G01N 21/5907* (2013.01); *G01N 21/8803* (2013.01)

(56) References Cited

U.S. PATENT DOCUMENTS

| | | | |
|---|---|---|---|
| 2004/0094853 | A1 | 5/2004 | Mbachu et al. |
| 2013/0213550 | A1* | 8/2013 | Berlin .................. C08L 97/00 156/62.2 |

FOREIGN PATENT DOCUMENTS

| | | |
|---|---|---|
| EP | 0336029 A1 | 10/1989 |
| EP | 2359996 A1 | 8/2011 |
| FR | 2 810 038 A1 | 12/2001 |
| JP | 2003-041225 A | 2/2003 |
| RU | 2 423 390 C2 | 7/2011 |
| WO | 00/39565 A1 | 7/2000 |
| WO | 02/071045 A2 | 9/2002 |
| WO | 2004/038390 A1 | 5/2004 |
| WO | WO 2008/035042 A1 | 3/2008 |
| WO | 2011/073531 A1 | 6/2011 |
| WO | 2012/136894 A1 | 10/2012 |
| WO | 2013/144453 A1 | 10/2013 |
| WO | 2013/144454 A1 | 10/2013 |

OTHER PUBLICATIONS

Communication pursuant to Article 94(3) EPC in related European Application No. 15 704 034.6.
Database WPI 2017, Week 201148; Thomson Scientific, London, GB, AN 2011-H79652 (Abstract of RU 2 423 390 C2) (1 page).
Communication Pursuant to Article 94(3) EPO in related European Patent Application No. 15 704 034.6, dated Mar. 27, 2018 (8 pages).

* cited by examiner

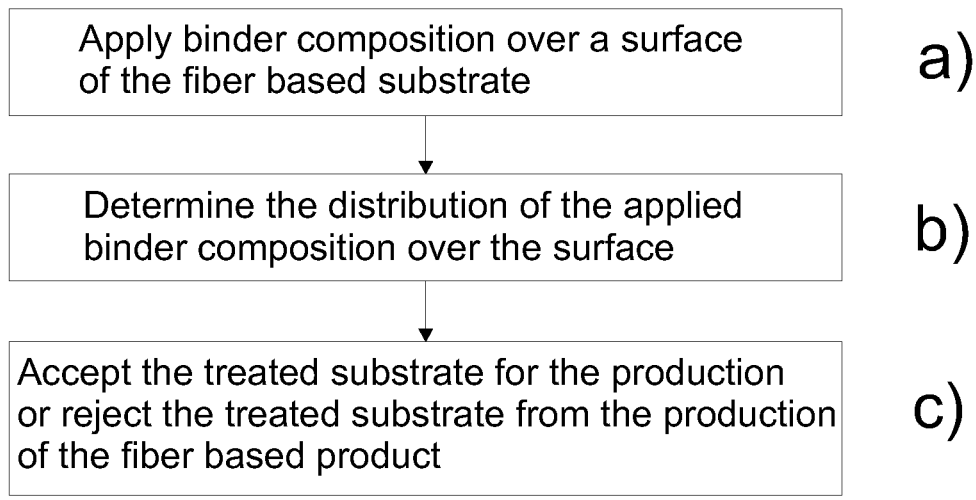

FIBER BASED PRODUCT

CROSS-REFERENCE TO RELATED APPLICATIONS

This application is a 35 U.S.C. § 371 National Phase Entry Application of International Application No. PCT/FI2015/050051 filed Jan. 27, 2015, which designated the U.S., and which claims priority to FI Application No. 20145090 filed Jan. 28, 2014, the contents of each of which are incorporated herein by reference in their entireties.

FIELD OF THE INVENTION

The invention relates to a method for producing a fiber based product, a method for producing a binder composition, a binder composition and a fiber based product.

BACKGROUND OF THE INVENTION

Modern production processes in wood industry have a very high production speed. This brings about high requirements for the reliability and effectiveness of quality control during the processes. It is well known that the traditional ways to monitor product defects during e.g. plywood production result in high reject rates of the final product due to the delay between the actual production and availability of quality testing results thereof. For glued or impregnated products the main sources of defects are related to the binder and its interaction with the substrate. Already small differences between different glue batches (e.g. viscosity or molecular weight distribution) or in the properties of the substrate (e.g. moisture content or density) will significantly change the adsorption and absorption behavior of the binder on and into the substrate. Consequently, gluing phase is the most challenging part in plywood production process. Problems in gluing can usually be seen only after hot pressing when it is already too late.

The inventors of the present invention have recognized a need for better systems to monitor the quality of the glued substrates on which binder composition has been applied. The current invention relates to a new method for producing a fiber based product, comprising a way to monitor the uniformity of the applied binder composition.

PURPOSE OF THE INVENTION

The purpose of the invention is to provide a new type of method for producing a fiber based product and to provide a method for producing a binder composition which allows for easy on-line monitoring of defects immediately after the gluing phase. The purpose of the invention is also to provide a new binder composition and a fiber based product.

SUMMARY

The method for producing a fiber based product according to the present invention is characterized by what is presented in claim 1.

BRIEF DESCRIPTION OF THE DRAWINGS

The accompanying drawing, which is included to provide a further understanding of the invention and constitutes a part of this specification, illustrates embodiments of the invention and together with the description helps to explain the principles of the invention. In the drawing:

FIG. 1 is a flow chart illustration of a method according to one embodiment of the present invention.

DETAILED DESCRIPTION OF THE INVENTION

The present invention relates to a method for producing a fiber based product comprising the steps of:

a) applying a binder composition over at least one surface of at least one fiber based substrate, which binder composition is prepared by using at least polymerizable substance, crosslinking agent, and colorant, and wherein the colorant is used in an amount such that the difference between the color of the binder composition and the color of a corresponding binder composition prepared without the use of the colorant, as measured on a Gardner scale, is at least 3 units;

b) determining the distribution of the applied binder composition over the entire at least one surface of the at least one fiber based substrate; and c) based on the determination in step b) either accepting the treated at least one fiber based substrate for the production of the fiber based product or rejecting the treated at least one fiber based substrate from the production of the fiber based product.

The inventors of the present invention surprisingly found out that adding a colorant into the binder composition in the amount according to the present invention facilitates determination of the distribution of the binder composition applied on a surface of the fiber based substrate. Especially, the inventors found out an efficient way to immediately check the distribution before proceeding into other production steps of fiber based product. This enhances the production process, because if the binder composition is uniformly applied over the desired surface of the fiber based substrate, the strength of the fiber based product is good. Information on the distribution on the binder composition at the early stage of the production of the fiber based product significantly reduces e.g. wood waste during the production process.

The present invention further relates to a method for producing a binder composition comprising the step of preparing the binder composition by using at least polymerizable substance, crosslinking agent, and colorant, wherein the colorant is used in an amount such that the difference between the color of the binder composition and the color of a corresponding binder composition prepared without the use of the colorant, as measured on a Gardner scale, is at least 3 units.

The corresponding binder composition is a reference binder composition. The corresponding binder composition is prepared in the corresponding way as the binder composition according to the present invention, except that the colorant is excluded. In case the preparation of the binder composition according to the present invention includes adding the colorant into a previously produced composition comprising cross-linking agent polymerized with polymerizable substance, the corresponding binder composition is prepared in the same way as the binder composition according to the present invention, except that the colorant is not added into the corresponding binder composition. In case the preparation of the binder composition according to the present invention includes polymerizing the polymerizable substance, the cross-linking agent and the colorant, the colorant is replaced, in the preparation of the corresponding binder composition, with the same amount of a polymerizable substance before the polymerization step.

The present invention further relates to a binder composition obtainable by the method according to the present invention.

The present invention further relates to a fiber based product comprising at least one fiber based substrate having a binder composition applied over at least one surface of the at least one fiber based substrate, which binder composition is prepared by using at least polymerizable substance, crosslinking agent, and colorant, wherein the colorant is used in an amount such that the difference between the color of the binder composition and the color of a corresponding binder composition prepared without the use of the colorant, as measured on a Gardner scale, is at least 3 units.

In one embodiment of the present invention the polymerizable substance is a compound selected from the class of phenols. In one embodiment of the present invention the polymerizable substance is selected from a group consisting of phenol, cresol, resorcinol and combinations thereof. In one embodiment of the present invention the polymerizable substance is phenol. In one embodiment of the present invention the polymerizable substance is selected from a group consisting of bio-based hydroxyphenols and their derivatives.

In one embodiment of the present invention the crosslinking agent is selected from a group of aldehydes. In one embodiment of the present invention the group of aldehydes comprises an aldehyde, a derivative of an aldehyde, an aldehyde forming compound and any combination thereof. In one embodiment of the present invention the derivative of an aldehyde is hexamethylenetetramine or trioxane. In one embodiment of the present invention the crosslinking agent is selected from a group consisting of an aromatic aldehyde, glyoxal, furfuryl alcohol, caprolactam and glycol compounds. The aromatic aldehyde can be furfuryl aldehyde. In one embodiment of the present invention the crosslinking agent is an aldehyde, and preferably formaldehyde, paraformaldehyde or a combination thereof.

In one embodiment of the present invention at least one catalyst is used for the production of the binder composition. In one embodiment of the present invention the catalyst is a base. In one embodiment of the present invention the catalyst is an alkali or an alkali earth hydroxide. In one embodiment of the present invention the catalyst comprises a salt or a hydroxide of an alkali metal. In one embodiment of the present invention the catalyst is selected from a group consisting of sodium hydroxide, potassium hydroxide and any mixture thereof. In one embodiment of the present invention the catalyst is an organic amine.

In one embodiment of the present invention, the at least one surface of at least one fiber based substrate is any part of the total surface area of the fiber based substrate. In one embodiment of the present invention, the at least one surface of at least one fiber based substrate is half of the total surface area of the fiber based substrate. In one embodiment of the present invention, the at least one surface of at least one fiber based substrate means various shapes on the surface of the fiber based substrate. In one embodiment of the present invention, the shape is a stripe or multiple stripes. In one embodiment of the present invention, the shape is a spot or multiple spots. By "the entire at least one surface" of the at least one fiber based substrate, it is meant the entire surface over which the binder composition has been applied. In other words, "the entire at least one surface" is not necessarily the total surface area of the fiber based substrate.

In one embodiment of the present invention the treated at least one fiber based substrate is, in step c), accepted for the production of the fiber based product when the applied binder composition is uniformly distributed over the entire surface, as visually determined.

In one embodiment of the present invention the treated at least one fiber based substrate is, in step c), accepted for the production of the fiber based product when the contrast value is 50% or less, wherein the contrast value is determined as $(D_s-D_t)/D_s \cdot 100\%$, wherein $D_s$ is the reflection density of the binder composition and $D_t$ is the reflection density of the surface of the at least one fiber based substrate having the binder composition applied thereon, as measured by reflection densitometry.

Reflection densitometry is the practice of characterizing the amount of light absorption of materials by measuring reflectance and calculating and reporting reflection density. Reflection density (D) is the light-absorbing property of a material, expressed as the logarithm of the reciprocal of the reflectance factor (R). Higher reflection density is an indication of more light absorbed. Reflection density is calculated as follows: $D=\log_{10}(1/R)=-\log_{10}(R)$. Reflection density of the fiber based substrate over which binder composition has been applied, is measured by using a reflection densitometer or spectrodensitometer according to ASTM standard test method for reflection density of printed matter (D7305-08a (Reapproved 2013)). Over a restricted range, the reflection density readings from a densitometer are approximately proportional to the binder composition film thickness, i.e. the uniformity of the applied binder composition.

Reflection densitometry can be used to determine whether the applied binder composition film is uniform by measuring the reflection density over a wide area. Multiple reflection density measurements are taken in specified positions on the surface over which binder composition has been applied in order to determine an average result. For example, five measurements are taken, one in each corner 25 mm from the edge of the surface over which the binder composition has been applied and one in the middle of the surface. The mean of the five readings is calculated. The contrast between the fiber based substrate over which the binder composition has been applied and the binder composition is determined. The contrast value is a measure of the uniformity of the binder composition layer on the surface of the fiber based substrate. A contrast value of 50% or less is acceptable.

In one embodiment of the present invention the colorant is used in an amount such that the difference between the color of the binder composition and the color of a corresponding binder composition prepared without the use of the colorant, as measured on a Gardner scale, is preferably at least 5 units, more preferably at least 7 units, and even more preferably at least 10 units.

In one embodiment of the present invention the colorant is used in an amount such that the difference between the color of the binder composition and the color of a corresponding binder composition prepared without the use of the colorant, as measured on a Gardner scale, is 3-18 units, preferably 10-18 units, and more preferably 14-17 units. The difference between the color of the binder composition and the color of a corresponding binder composition could also be higher than 18 units, but the upper limit of the Gardner scale is 18 units.

In one embodiment of the present invention the fibers of the fiber based substrate are synthetic or natural fibers. Synthetic fibers are made from synthesized polymers or small molecules. Natural fibers are made from plant, animal and mineral sources. In one embodiment of the present invention the fibers of the fiber based substrate are wood based natural fibers.

In one embodiment of the present invention the fiber based substrate is a veneer. In one embodiment of the present invention the fiber based substrate is wood or wood containing material. In one embodiment of the present invention the fiber based substrate is a cellulose based timber product. In one embodiment of the present invention the fiber based substrate is a gluelam product.

In one embodiment of the present invention the binder composition is applied over at least one surface of at least two veneers and the at least two veneers are glued together with the binder composition. In one embodiment of the present invention at least two veneers are glued together with the binder composition under the influence of hot pressing.

In one embodiment of the present invention the veneer is made of softwood. In one embodiment of the present invention the veneer is made of hardwood.

In one embodiment of the present invention the veneer is selected from a group consisting of pine veneer, poplar veneer, beech veneer, spruce veneer, and birch veneer. In one embodiment of the present invention the veneer is spruce veneer or pine veneer. In one embodiment of the present invention the veneer is birch veneer.

In one embodiment of the present invention step a) comprises applying 80-250 g, and more preferably 100-200 g of binder composition per square meter of veneer. The amount of binder composition applied per square meter of veneer according to the present invention results in good contact between the binder composition and the veneer, which leads to a good strength and wood failure value of the fiber based product.

In one embodiment of the present invention the fiber based substrate is a wood chip, paper, cardboard, or cotton. Wood chip is a piece of wood formed by cutting or chipping large pieces of wood. The size of wood chips may vary.

In one embodiment of the present invention the fiber based substrate comprises organic fibers, inorganic fibers, plastic fibers, glass fibers, carbon fibers, or any combination thereof. In one embodiment of the present invention the fiber based substrate comprises or consists of mineral wool. In one embodiment of the present invention the fiber based substrate comprises or consists of rock wool. In one embodiment of the present invention the fiber based substrate comprises or consists of rubber, polyamide, or polyester. In one embodiment of the present invention the fiber based substrate comprises or consists of vulcanized fiber.

In one embodiment of the present invention the polymerizable substance, the crosslinking agent and the colorant are polymerized. In one embodiment of the present invention the step of preparing the binder composition comprises the step of polymerizing the polymerizable substance, the crosslinking agent and the colorant. In one embodiment of the present invention the binder composition according to the present invention is prepared by forming an aqueous composition comprising colorant, polymerizable substance and crosslinking agent, and by allowing polymerization reactions to take place between these reactant components under the influence of heating the composition. In one embodiment of the present invention the binder composition according to the present invention is prepared by mixing colorant with a previously produced composition comprising crosslinking agent polymerized with polymerizable substance.

In one embodiment of the present invention the aqueous composition comprising at least polymerizable substance and crosslinking agent is heated at a temperature of 30-95° C. for allowing polymerization reactions to take place, until a binder composition with a viscosity value of 80-1200 cp is formed.

In one embodiment of the present invention the aqueous composition comprising at least polymerizable substance, crosslinking agent, and colorant is heated at a temperature of 30-95° C. for allowing polymerization reactions to take place, until a binder composition with a viscosity value of 80-1200 cp is formed.

In one embodiment of the present invention the colorant is a phenolic compound, preferably a wood-based phenolic compound, and more preferably lignin or tannin. Wood-based phenolic compounds, especially lignins and tannins, have a similar chemical structure as the PF resin. Therefore, a homogeneous dispersion of components is formed, in which at least part of the components are solubilized. The formation of a homogeneous dispersion minimizes phase separation of the components.

In this specification, unless otherwise stated, the expression "lignin" should be understood as lignin originating from any suitable lignin source. The lignin may include essentially pure lignin. By the expression "essentially pure lignin" should be understood as at least 90% pure lignin, preferably at least 95% pure lignin. In one embodiment of the present invention the essentially pure lignin comprises at most 10%, preferably at most 5%, of other components. Extractives and carbohydrates such as hemicelluloses can be mentioned as examples of such other components. In one embodiment of the present invention the lignin contains less than 10 weight-%, preferably less than 6 weight-%, and more preferably less than 4 weight-% of carbohydrates. The amount of carbohydrates present in lignin can be measured by high performance anion exchange chromatography with pulsed amperometric detector (HPAE-PAD) in accordance with standard SCAN-CM 71.

In one embodiment of the present invention the ash percentage of lignin is less than 7.5 weight-%, preferably less than 5 weight-%, and more preferably less than 3 weight-%. The ash content can be determined by carbonifying and quickly burning a lignin sample so that alkali salts are not melted before the organic matter has been burned (e.g. 20-200° C. for 30 minutes, after which temperature is adjusted to 200-600° C. for 1 h, and thereafter adjusting the temperature to 600-700° C. for 1 hour), and finally the lignin sample is ignited at 700° C. for 1 h. Ash content of a lignin sample refers to the mass that remains of the sample after burning and ignition, and it is presented as percent of the sample's dry content.

In one embodiment of the present invention the lignin is selected from a group consisting of kraft lignin, steam explosion lignin, biorefinery lignin, supercritical separation lignin, hydrolysis lignin, flash precipitated lignin, biomass originating lignin, lignin from alkaline pulping process, lignin from soda process, lignin from organosols pulping and combinations thereof. In one embodiment of the present invention the lignin is wood based lignin. The lignin can originate from softwood, hardwood, annual plants or from a combination thereof.

In one embodiment of the present invention the lignin is Kraft lignin. By "kraft lignin" is to be understood in this specification, unless otherwise stated, lignin that originates from kraft black liquor. Black liquor is an alkaline aqueous solution of lignin residues, hemicellulose, and inorganic chemicals used in a kraft pulping process. The black liquor from the pulping process comprises components originating from different softwood and hardwood species in various proportions. Lignin can be separated from the black liquor by different, techniques including e.g. precipitation and filtration. Lignin usually begins precipitating at pH values below 11-12. Different pH values can be used in order to precipitate lignin fractions with different properties. These lignin fractions differ from each other by molecular weight distribution, e.g. Mw and Mn, polydispersity, hemicellulose and extractive contents. The molar mass of lignin precipitated at a higher pH value is higher than the molar mass of lignin precipitated at a lower pH value. Further, the molecular weight distribution of lignin fraction precipitated at a lower pH value is wider than of lignin fraction precipitated at a higher pH value. The precipitated lignin can be purified from inorganic impurities, hemicellulose and wood extractives using acidic washing steps. Further purification can be achieved by filtration.

In one embodiment of the present invention the lignin is flash precipitated lignin. The term "flash precipitated lignin" should be understood in this specification as lignin that has been precipitated from black liquor in a continuous process by decreasing the pH of a black liquor flow, under the influence of an over pressure of 200-1000 kPa, down to the precipitation level of lignin using a carbon dioxide based acidifying agent, preferably carbon dioxide, and by suddenly releasing the pressure for precipitating lignin. The method for producing flash precipitated lignin is disclosed in patent application FI 20106073. The residence time in the above method is under 300 s. The flash precipitated lignin particles, having a particle diameter of less than 2 μm, form agglomerates, which can be separated from black liquor using e.g. filtration. The advantage of the flash precipitated lignin is its higher reactivity compared to normal kraft lignin. The flash precipitated lignin can be purified and/or activated if needed for the further processing.

In one embodiment of the present invention the lignin is separated from pure biomass. The separation process can begin with liquidizing the biomass with strong alkali followed by a neutralization process. After the alkali treatment the lignin can be precipitated in a similar manner as presented above. In one embodiment of the present invention the separation of lignin from biomass comprises a step of enzyme treatment. The enzyme treatment modifies the lignin to be extracted from biomass. Lignin separated from pure biomass is sulphur-free.

In one embodiment of the present invention the lignin is steam explosion lignin. Steam explosion is a pulping and extraction technique that can be applied to wood and other fibrous organic material.

By "biorefinery lignin" is to be understood in this specification, unless otherwise stated, lignin that can be recovered from a refining facility or process where biomass is converted into fuel, chemicals and other materials.

By "supercritical separation lignin" is to be understood in this specification, unless otherwise stated, lignin that can be recovered from biomass using supercritical fluid separation or extraction technique. Supercritical conditions correspond to the temperature and pressure above the critical point for a given substance. In supercritical conditions, distinct liquid and gas phases do not exist. Supercritical water or liquid extraction is a method of decomposing and converting biomass into cellulosic sugar by employing water or liquid under supercritical conditions. The water or liquid, acting as a solvent, extracts sugars from cellulose plant matter and lignin remains as a solid particle.

In one embodiment of the present invention the lignin is hydrolysis lignin. Hydrolysed lignin can be recovered from paper-pulp or wood-chemical processes.

In one embodiment of the present invention the lignin originates from an organosols process. Organosolv is a pulping technique that uses an organic solvent to solubilize lignin and hemicellulose.

In one embodiment of the present invention, the lignin is alkalated lignin. In one embodiment of the present invention, alkalated lignin is prepared before the preparation of the binder composition according to the present invention.

In one embodiment of the present invention alkalated lignin is prepared using the following method, comprising the steps of:

i) forming, under heating at a temperature of 30-98° C., an aqueous dispersion comprising alkali and lignin, wherein the alkali comprises a hydroxide of an alkali metal; and ii) heating the dispersion formed in step a) at a temperature of 50-95° C.

In one embodiment of the present invention the alkali is selected from a group consisting of sodium hydroxide, potassium hydroxide and a mixture thereof. In one embodiment of the present invention the alkali is sodium hydroxide. In one embodiment of the present invention the concentration of alkali is 5-50 weight-%, and preferably 10-25 weight-% based on the total weight of the dispersion in step i). In one embodiment of the present invention the concentration of lignin in step i) is 10-50 weight-%, preferably 20-50 weight-%, and more preferably 20-45 weight-% based on the total weight of the dispersion in step i). In one embodiment of the present invention step i) is carried out preferably at a temperature of 30-80° C., and more preferably at a temperature of 30-70° C. In one embodiment of the present invention step i) is carried out preferably at a temperature of 71-94° C. In one embodiment of the present invention step ii) is carried out for 15 minutes-24 hours, preferably for no longer than 5 hours, and more preferably for 0.5-1.5 hours.

Alkalated lignin has an increased reactivity as compared to untreated lignin or so-called raw lignin. Without limiting the invention to any specific theory about why step i) and step ii) results in a more reactive lignin being formed, it is to be considered that these steps result in the macromolecular structure of lignin being opened whereby the steric hindrances that usually disable reactive groups in lignin structures are removed. These steps, or a so-called alkalation process, may also add charged groups to the lignin macromolecule. The advantage of using alkalated lignin e.g. for producing a binder composition is that the compatibility and reaction behavior is much better than in a normal case, where non-treated lignin has been used in the cooking or polymerizing stage.

In one embodiment of the present invention the tannin used originates from any wood species. Tannin may originate from e.g. bark or heartwood. Quebracho tree, beech tree and wattle tree are presented as examples of possible sources of tannin.

In one embodiment of the present invention the tannin used originates from softwood bark. In one embodiment of the present invention the tannin is separated from softwood bark of debarking units in sawmills or pulp mills. The separation process can be combined with an ethanol extraction process, a hot water extraction process, a hot steam extraction process or a water-ethanol extraction process of softwood bark.

In one embodiment of the present invention the tannin is condensed tannin. Condensed tannin has a high dry content and is therefore suitable to be used in the present invention. The dry matter content of condensed tannin may vary between 40-100% and is suitably between 60-90% and preferably between 70-80%. Tannin with such dry matter content can easily be dispersed, whereby a good reactivity with the other reactant components is achieved. The tannin may also be hydrolysable tannin.

In one embodiment of the present invention the colorant is lignin and the lignin has a weight average molecular weight of 500-10000 g/mol, and preferably of 2000-8000 g/mol.

In one embodiment of the present invention the colorant is lignin and the polydispersity index of lignin is 1.5-15, preferably 2-13, and more preferably 3-9. The polydispersity index range of 3-9 results in less variation in the preparation of the binder composition and thus makes it easier to control the preparation of the binder composition.

In one embodiment of the present invention the colorant is tannin and the tannin has a weight average molecular weight of 1000-4000 g/mol, and preferably of 1300-3000 g/mol.

In one embodiment of the present invention the colorant is tannin and the polydispersity index of tannin is 1-6, preferably 1.1-4, and more preferably 1.5-3. The polydispersity index range of 1.5-3 results in less variation in the preparation of the binder composition and thus makes it easier to control the preparation of the binder composition.

When lignin or tannin of the weight average molecular weight range and polydispersity index range according to the present invention is used as a colorant, the binder composition partly penetrates into the veneer and partly stays on the surface of the veneer. Thus, the strength of the plywood prepared from the veneer is good.

The molecular weight of the lignin or tannin can be determined by using a high-performance size-exclusion chromatography.

In one embodiment of the present invention, the molecular weight of the lignin or tannin is determined by using a high-performance size-exclusion chromatography in the following manner: Two parallel measurements are carried out. 0.1 M NaOH is used as an eluent. Calibration is done using Na-polystyrene sulfonate standards having a molecular weight of 1100-73900 g/mol. For quality control, standard quality kraft lignin and PSS molecular weight standard are used. The columns used are PSS MCX precolumns, 1000 Å and 100 000 Å separation columns filled with sulfonated styrene-divinylbenzene copolymer matrix. Isocratic run program is used. The run time is 45 minutes. The injection volume is 50 µl. The flux is 0.5 ml per minute. The temperature is 25° C. As a result of the chromatography, number average molecular weight (Mn), weight average molecular weight (Mw), peak molecular weight (Mp) and polydispersity index (PDI) values can be reported.

The polydispersity index (PDI) can be determined by size-exclusion high-performance liquid chromatography (SEC-HPLC). The polydispersity index (PDI) is a measure of the distribution of molecular mass in a given polymer sample. The PDI is calculated as the weight average molecular weight divided by the number average molecular weight. PDI indicates the distribution of individual molecular masses in a batch of polymers. The higher the polydispersity index of colorant, the wider the molecular weight distribution range of the colorant.

In one embodiment of the present invention the colorant is flavone dye, iso-quinoline dye, polyene colorant, pyran colorant, chromene dye, naphthochinone dye, chinone dye, anthrachinone dye, chromene dye, benzophyrone dye, indigoid dye or indole colorant.

In one embodiment of the present invention the fiber based substrate is a wood board and the binder composition is at least partly absorbed into the at least one surface of the at least one wood board.

In one embodiment of the present invention the applied binder composition is uniformly distributed over the entire at least one surface of the at least one fiber based substrate, as visually determined.

In one embodiment of the present invention the contrast value is 50% or less, and the contrast value is determined as $(D_s-D_t)/D \cdot 100\%$, wherein $D_s$ is the reflection density of the binder composition and $D_t$ is the reflection density of the surface of the at least one fiber based substrate having the binder composition applied thereon, as measured by reflection densitometry.

In one embodiment of the present invention the fiber based product is plywood and the average wood failure of the plywood is above 60%, preferably above 70%, and more preferably above 80%. Wood failure is a measure of the strength of the binder composition. Wood failure is determined in accordance with standard EN314-1.

In one embodiment of the present invention 80-250 g, and more preferably 100-200 g of binder composition is applied per square meter of veneer.

In one embodiment of the present invention the fiber based substrate is a wood chip.

In one embodiment of the fiber based product, the binder composition is obtained by the method according to the present invention.

The embodiments of the invention described hereinbefore may be used in any combination with each other. Several of the embodiments may be combined together to form a further embodiment of the invention.

The methods, the binder composition or the fiber based product, to which the invention is related, may comprise at least one of the embodiments of the invention described hereinbefore.

An advantage of the method according to the present invention is that the method allows for a simple and fast determination of the distribution of the binder composition over a surface of the fiber based substrate during the production process of fiber based products. This is due to the high contrast between the color of the binder composition and the color of the fiber based substrate. Consequently, the method enhances the overall production process of fiber based products. The distribution of the binder composition can be determined on-line, which assists in detecting the gluing or impregnation defects. As a result, the amount of e.g. wood waste is reduced. The method also improves the quality of the final product, because the uniformity of the binder composition film applied on the fiber based substrate affects the final product strength.

EXAMPLES

Reference will now be made in detail to the embodiments of the present invention, an example of which is illustrated in the accompanying drawing.

The description below discloses some embodiments of the invention in such a detail that a person skilled in the art is able to utilize the invention based on the disclosure. Not all steps of the embodiments are discussed in detail, as many of the steps will be obvious for the person skilled in the art based on this specification.

FIG. 1 illustrates a method according to one embodiment of the present invention for producing a fiber based product.

Before applying the binder composition over at least one surface of at least one fiber based substrate, the binder composition is prepared. At least polymerizable substance, crosslinking agent and colorant are used for the preparation of the binder composition. Also other components can be used for the preparation of the binder composition. The colorant is used in such an amount that it results in at least 3 units difference between the color of the binder composition and the color of a corresponding reference binder composition. The reference binder composition is prepared under the same reaction conditions and using the same component amounts as the binder composition according to the present invention, except that the colorant is excluded from the preparation of the reference binder composition. The color of the binder composition and the reference binder composition are measured on a Gardner scale.

The binder composition prepared as described above is then applied over at least one surface of at least one fiber based substrate. The binder composition may be applied over the total surface area of the fiber based substrate. The binder composition may also be applied over certain areas on the surface of the fiber based substrate. Such areas may be shaped like stripes, spots, or any other shape.

After the application of the binder composition over the surface of the fiber based substrate, the distribution of the applied binder composition over the entire surface that was intended to be covered is determined. The determination can be done visually. The determination can also be done by determining the contrast value as described in the description above.

The treated fiber based substrate is then either accepted for the production of the fiber based product or rejected from the production of the fiber based product, based on the determination step described above.

Example 1

Preparing a Binder Composition

In this example a lignin phenol formaldehyde (LPF) binder composition was produced.
The following components and their amounts were used:

| Material | Concentration (%) | Mass (g) |
|---|---|---|
| NaOH | 50 | 80 |
| Water | | 145 |
| Kraft lignin | 73 | 205 |
| Formaldehyde | 40 | 475 |
| Phenol | 90 | 300 |

In this example, and examples 2 and 7, the molecular weight distribution of lignin was determined by SEC-HPLC and the weight average molecular weight of the lignin used in these examples was 4000-6000 g/mol. The polydispersity index of the lignin used in these examples was determined by SEC-HPLC and the polydispersity index of the lignin used in these examples was 4-6.

Firstly, a synthetic phenol formaldehyde (PF) binder composition was produced by polymerizing phenol and formaldehyde in the presence of water and sodium hydroxide (NaOH) as a catalyst. Formaldehyde was added in a stepwise manner to an aqueous phenol composition and thereafter the temperature of the formed composition was increased up to 80-90° C. The composition was cooked at this temperature until a viscosity value of 295 cP was reached. The viscosity was measured at 25° C. using a rotary viscometer. To this composition, the lignin used as a colorant was physically mixed.

The lignin may also be alkalated lignin. Alkalated lignin can be prepared as described in Example 2.

The molecular weight distribution of the formed binder composition was determined by SEC-HPLC. According to the results, the weight average molecular weight of the formed binder composition was 900-10000 g/mol.

The polydispersity index of the formed binder composition was determined by SEC-HPLC. According to the results, the polydispersity index of the formed binder composition was 7.

The color difference of the binder composition formed as described above and the corresponding binder composition formed similarly except without the addition of lignin, was determined on Gardner scale as described in Example 3. According to the results, the color difference was 10 units, as measured on Gardner scale.

The binder composition formed as above indicated was further used for the production of fiber based product.

Example 2

Preparing a Binder Composition

In this example a LPF binder composition was produced. The following components and their amounts were used:

| Material | Concentration (%) | Mass (g) |
|---|---|---|
| NaOH | 50 | 103 |
| Water | | 136 |
| Kraft lignin | 73 | 145 |
| Formaldehyde | 37 | 268 |
| Phenol | 90 | 118 |

Firstly, alkalated lignin was prepared as follows. Water and part of the sodium hydroxide (65 g) were mixed and heating of the mixture was started. Then lignin was dispersed slowly into the mixture of sodium hydroxide and water with agitation and simultaneously the temperature was increased up to 60° C. When all of the lignin had been dispersed, the dispersion was heated at a temperature of about 76° C. for about 1 hour.

Then the phenol was added in a stepwise manner to the above formed composition containing alkalated lignin, followed by the addition of the first part of the formaldehyde (125 g) also in a stepwise manner. The formed composition was then cooked at a temperature of 70-80° C. for allowing the reactant components therein to react with each other. During this step of cooking the composition, the second part of the formaldehyde (143 g) was added to the composition. After adding formaldehyde into the composition, the composition was cooked for ten more minutes, after which the last part of catalyst, NaOH (38 g), was added to the composition. Again, the composition was allowed to cook at a temperature of about 80-90° C. for about 2 hours and 47 minutes, after which the process was ended by cooling down the reaction composition.

The molecular weight distribution of the formed binder composition was determined by SEC-HPLC. According to the results, the weight average molecular weight of the formed binder composition was 11000-12000 g/mol.

The polydispersity index of the formed binder composition was determined by SEC-HPLC. According to the results, the polydispersity index of the formed binder composition was 8.

The color difference of the binder composition formed as described above and the corresponding binder composition formed similarly except without the addition of alkalated lignin, was determined on Gardner scale as described in Example 3. In the corresponding binder composition, alkalated lignin was replaced with the same amount of phenol before the polymerization step. According to the results, the color difference was 17 units, as measured on Gardner scale.

The binder composition formed as above indicated was further used for the production of fiber based product.

Example 3

Coloring of PF Binder Composition with Lignin and the Analysis of Color Change on Gardner Scale The aim of this test was to create a method to evaluate the color of a reference binder composition (phenol formaldehyde binder composition, PF binder composition) and in addition to evaluate the color change in the binder composition induced by the addition of lignin or alkalated lignin (lignin phenol formaldehyde binder composition, LPF binder composition).

The LPF binder composition (sample 8) was prepared as described in Example 2. The PF binder composition (sample 0, reference) was prepared in a corresponding manner except that alkalated lignin was replaced with the same amount of phenol before the polymerization step.

The binder compositions were diluted with water to a concentration of 1 g (dry mass of binder composition)/l. Diluted binder composition was placed in a test tube and the color of the dilution was visually determined by comparing the color of the dilution with the color of Gardner laboratories reference samples.

Alkalated lignin or non-alkalated lignin (dry lignin) were then added to diluted PF binder composition according to table 2 in a concentration of 10 g/l. The lignin content of alkalated lignin was 30%. The samples and their description are presented in table 1.

The solution was then also diluted to a concentration of 1 g/l. The color of the solution was visually determined by comparing the color of the solution with the color of Gardner laboratories reference samples. The color of the binder composition with or without lignin addition is presented in table 2.

TABLE 1

Samples and their description

| Sample | Description |
| --- | --- |
| 0 | Reference |
| 1 | Alkalated 1 |
| 2 | Alkalated 2 |
| 3 | Alkalated 3 |
| 4 | Alkalated 4 |
| 5 | Alkalated 5 |
| 6 | Dry lignin 1 |
| 7 | Dry lignin 2 |
| 8 | Lignin polymerized to PF binder composition |

TABLE 2

Lignin and alkalated lignin amounts and the results of the color measurements

| Sample | Dry binder composition (g) | Phenol in diluted sample (g) | Added alkalated lignin (g) | Added dry lignin (g) | Lignin/Phenol (%) | Value on Gardner scale |
| --- | --- | --- | --- | --- | --- | --- |
| 0 | 1 | 0.5 | 0 | 0 | 0 | <1 |
| 1 | 1 | 0.5 | 0.17 | 0 | 10 | 3 |
| 2 | 1 | 0.5 | 0.5 | 0 | 30 | 5 |
| 3 | 1 | 0.5 | 0.83 | 0 | 50 | 10 |
| 4 | 1 | 0.5 | 1.67 | 0 | 100 | 13 |
| 5 | 1 | 0.5 | 3.33 | 0 | 200 | 18 |
| 6 | 1 | 0.5 | 0 | 0.1 | 20 | 3 |
| 7 | 1 | 0.5 | 0 | 0.15 | 30 | 6 |
| 8 | 1 | 0.5 | 0 | 0 | 50 | 18 |

According to the results, the addition of lignin changed the color of the diluted binder composition. The change was noted immediately after the addition of alkalated lignin and when dry lignin powder was dispersed in binder composition. Further according to the results, the addition of dry or alkalated lignin gave similar response on Gardner scale. Samples 1 and 6 were not accepted for production of fiber based product, because the difference of the color of the binder composition and the color of the corresponding reference binder composition (sample 0) was less than 3 units.

Example 4

Coloring of PF Binder Composition with Tannic Acid and the Analysis of Color Change on Gardner Scale The aim of this test was to evaluate the color change in binder composition induced by addition of tannic acid.

The PF binder composition was prepared as described in Example 1.

Binder composition was diluted with water to a concentration of 1 g (dry mass of resin)/l. Diluted binder composition was placed in a test tube and the color of the dilution was visually determined by comparing the color of the dilution with the color of Gardner laboratories reference samples.

Tannic acid (CAS: 1401-55-4, $C_{76}H_{52}O_{46}$), which is a specific type of tannin, was then added to diluted PF binder composition according to table 3. To 1 g of binder composition 0, 1, 2 or 4 g of tannic acid was added and the solution was mixed. The molecular weight distribution of the tannic acid was determined by SEC-HPLC and the weight average molecular weight of the tannic acid used was 1700 g/mol. The polydispersity index of the tannic acid used in this example was determined by SEC-HPLC and the polydispersity index of the tannic acid used was 1.5.

The solution was then diluted to a concentration of 1 g/l. The color of the solution was visually determined by comparing the color of the solution with the color of Gardner laboratories reference samples. The color of the binder composition with or without tannic acid addition is presented in table 3. The dry matter content (DMC) of the binder composition was determined by heating the sample at a temperature of 60° C. for 6 hours.

TABLE 3

Tannic acid amounts and the results of the color measurement

| Sample | Dry binder composition (g) | Binder composition DMC (%) | Diluted binder composition (g) | Tannin/Phenol (%) | Added tannin (g) | Value on Gardner scale |
|---|---|---|---|---|---|---|
| 0 | 1 | 45.8 | 2.2 | 0 | 0 | <1 |
| 1 | 1 | 45.8 | 2.2 | 200 | 1 | 3 |
| 2 | 1 | 45.8 | 2.2 | 400 | 2 | 6 |
| 3 | 1 | 45.8 | 2.2 | 800 | 4 | 11 |

According to the results, the addition of tannic acid changed the color of the diluted binder composition. The change was noted immediately after the addition of tannic acid into the binder composition. Sample 1 was not accepted for production of fiber based product, because the difference of the color of the binder composition and the color of the corresponding reference binder composition (sample 0) was less than 3 units.

Example 5

Coloring of PF Binder Composition with Flavone Dye Quercitrin and the Analysis of Color Change on Gardner Scale The aim of this test was to evaluate the color change in binder composition induced by the addition of flavone dye quercitrin.

The PF binder composition was prepared as described in Example 1.

Binder composition was diluted with water to a concentration of 1 g (dry mass of resin)/l. Diluted binder composition was placed in a test tube and the color of the dilution was visually determined by comparing the color of the dilution with the color of Gardner laboratories reference samples.

Quercitrin dye (CAS: 522-12-3) was then added to diluted PF binder composition according to table 4. To 1 g of binder composition 0, 0.5, 1 or 2 g of quercitrin dye was added and the solution was mixed.

The solution was then diluted to a concentration of 1 g/l. The color of the solution was visually determined by comparing the color of the solution with the color of Gardner laboratories reference samples. The color of the binder composition with or without quercitrin dye addition is presented in table 4.

TABLE 4

Quercitrin dye amounts and the results of the color measurement

| Sample | Dry binder composition (g) | Binder composition DMC (%) | Diluted binder composition (g) | Added quercitrin dye (g) | Value on Gardner scale |
|---|---|---|---|---|---|
| 0 | 1 | 45.8 | 2.2 | 0 | <1 |
| 1 | 1 | 45.8 | 2.2 | 0.5 | 3 |
| 2 | 1 | 45.8 | 2.2 | 1 | 5 |
| 3 | 1 | 45.8 | 2.2 | 2 | 8 |

According to the results, the addition of quercitrin dye significantly changed the color of the diluted binder composition. The change was noted immediately after the addition of quercitrin dye into the binder composition. Sample 1 was not accepted for production of fiber based product, because the difference of the color of the binder composition and the color of the corresponding reference binder composition (sample 0) was less than 3 units.

Instead of quercitrin dye, any other colorant, such as iso-quinoline dye, polyene colorant, pyran colorant, chromene dye, naphthochinone dye, chinone dye, anthrachinone dye, chromene dye, benzophyrone dye, indigoid dye or indole colorant, may similarly be used as the colorant.

Example 6

The Use of a Binder Composition for Producing Plywood

The binder composition of Example 1 or Example 2 was used in the production of plywood. Spruce veneer was used.

The binder composition was applied over the surface of at least one side of the veneers. The distribution of the applied binder composition over the surface of the veneer was determined as follows. The reflection density ($D_t$) of the surface, on which the binder composition was applied, was measured by reflection densitometry according to ASTM standard test method for reflection density of printed matter (D7305-08a (Reapproved 2013)). Five separate measurements were taken in each corner and in the middle of the surface over which the binder composition had been applied. The mean of the five measurements were calculated. The reflection density of the binder composition ($D_s$) was also measured by reflection densitometry. The contrast value was determined as $(D_s-D_t)/D \cdot 100\%$. The contrast value was 20% when the binder composition of Example 1 was used, and 15% when the binder composition of Example 2 was used. The contrast value was found acceptable and the treated veneers were accepted for the production of plywood.

The accepted veneers were used in plywood production in the following manner. The wood veneers were joined together by the binder composition to form plywood. The wood veneers with the binder composition were pressed by hot-pressing technique. The plywood hot-pressing temperature used was about 130° C. For determining the optimum hot-pressing time needed for the different plywood, the temperature rise of the innermost glue line of the plywood panel was followed. The hot-pressing time was the time it took to reach 100° C., plus two minutes for curing the binder composition.

Example 7

Preparing a Binder Composition and Applying the Binder Composition on Rock Wool

First, a LPF binder composition was produced. The following components and their amounts were used.

| Material | Concentration (%) | Mass (g) |
|---|---|---|
| NaOH | 50 | 110 |
| Water | | 225 |
| Lignin | 70 | 170 |
| Formaldehyde | 37 | 1090 |
| Phenol | 90 | 535 |
| Urea | 100 | 110 |
| Borax | 100 | 45 |
| Boric acid | 100 | 25 |

Firstly, water, sodium hydroxide, phenol and lignin were mixed. Then, borax was added to the dispersion and the components were allowed to react for one hour at 50° C. Formaldehyde was then added and the dispersion was heated at a temperature of 65° C. for 2.5 hours. The dispersion was then allowed to cool to 40° C. and boric acid and urea were added, respectively.

The lignin may also be alkalated lignin. Alkalated lignin can be prepared as described in Example 2.

The molecular weight distribution of the formed binder composition was determined by SEC-HPLC. According to the results, the weight average molecular weight of the formed binder composition was 5000-6500 g/mol.

The polydispersity index of the formed binder composition was determined by SEC-HPLC. According to the results, the polydispersity index of the formed binder composition was 7.5.

The color difference of the binder composition formed as described above and the corresponding binder composition formed similarly except without the addition of lignin, was determined on Gardner scale as described in Example 3. In the corresponding binder composition, lignin was replaced with the same amount of phenol before the polymerization step. According to the results, the color difference was 16 units, as measured on Gardner scale.

The binder composition formed as above indicated was then applied on rock wool as follows. Mixture of volcanic stones and coke were fed to a furnace. The melt was allowed to run out of the bottom of the furnace onto the spinning machine, where fibers of rock wool were spun to give rock wool with a fiber-like structure. The spinning was continued while minor amounts of binder composition prepared as above and oil were sprayed on the individual fibers of rock wool, i.e. the fiber based substrate, in order to apply the binder composition on rock wool. The rock wool fibers, on which the binder composition was applied, were then collected on a belt conveyor.

The distribution of the applied binder composition over the entire surface of the rock wool fibers was determined by visually detecting that the surface of the fibers was colored. According to the visual determination the rock wool was accepted for the production of the fiber based product, i.e. a cured rock wool mat.

Example 8

Applying a Binder Composition on Wood Chips

The binder composition of Example 1 or Example 2 was applied on wood chips.

The binder composition was applied over at least one surface of the wood chip. The distribution of the applied binder composition over the entire surface of the wood chip was determined as described in Example 5.

The contrast value was 30% when the binder composition according to Example 1 was used and 15% when the binder composition according to Example 2 was used. The contrast value was found acceptable and the treated wood chips were accepted for the production of fiber based product.

It is obvious to a person skilled in the art that with the advancement of technology, the basic idea of the invention may be implemented in various ways. The invention and its embodiments are thus not limited to the examples described above; instead they may vary within the scope of the claims.

The invention claimed is:

1. A method for producing a fiber based product, the method comprising:
   a) applying a binder composition over at least one surface of at least one fiber based substrate to provide a treated at least one fiber based substrate, wherein the fiber based substrate is a veneer, a wood chip, paper, cardboard, or cotton, the binder composition prepared by using at least a polymerizable substance, a crosslinking agent, and a colorant comprising lignin, wherein the colorant is used in an amount such that the difference between a color of the binder composition and a color of a corresponding binder composition prepared without the use of the colorant, as measured on a Gardner scale, is at least 3 units;
   b) calculating the distribution of the applied binder composition over the entire at least one surface of the at least one fiber based substrate; and
   c) accepting the treated at least one fiber based substrate for the production of the fiber based product when contrast value is 50% or less, or rejecting the treated at least one fiber based substrate from the production of the fiber based product when the contrast value is greater than 50%, wherein the contrast value is defined as $(D_s-D_t)/D_s*100\%$, wherein $D_s$ is a reflection density of the binder composition, and $D_t$ is a reflection density of the surface of the treated at least one fiber based substrate, as measured by reflection densitometry.

2. The method of claim 1, wherein the colorant is used in an amount such that the difference between the color of the binder composition and the color of a corresponding binder composition prepared without the use of the colorant, as measured on a Gardner scale, is at least 5 units.

3. The method of claim 1, wherein the polymerizable substance, the cross-linking agent and the colorant are polymerized.

4. The method of claim 1, wherein the lignin has a weight average molecular weight of 500-10000 g/mol.

5. The method of claim 1, wherein the poly-dispersity index of the lignin is 1.5-15.

* * * * *

UNITED STATES PATENT AND TRADEMARK OFFICE
CERTIFICATE OF CORRECTION

PATENT NO. : 10,293,516 B2  
APPLICATION NO. : 15/114150  
DATED : May 21, 2019  
INVENTOR(S) : Suvi Pietarinen et al.

Page 1 of 1

It is certified that error appears in the above-identified patent and that said Letters Patent is hereby corrected as shown below:

On the Title Page

At Item (30) "Foreign Application Priority Data", please insert --Jan. 28, 2014, (FI) 20145090--.

Signed and Sealed this
Second Day of July, 2019

Andrei Iancu
*Director of the United States Patent and Trademark Office*